United States Patent [19]

Schmidt

[11] 4,393,256

[45] Jul. 12, 1983

[54] HYDRATION OF OLEFINS

[75] Inventor: Robert J. Schmidt, Rolling Meadows, Ill.

[73] Assignee: UOP Inc., Des Plaines, Ill.

[21] Appl. No.: 332,042

[22] Filed: Dec. 17, 1981

[51] Int. Cl.³ .................... C07C 29/06; C07C 29/00; C07C 31/08; C07C 31/10
[52] U.S. Cl. .................................. 568/907; 568/886; 568/888; 568/889; 568/890
[58] Field of Search ............... 568/907, 889, 890, 886, 568/888

[56] References Cited

U.S. PATENT DOCUMENTS

| | | | |
|---|---|---|---|
| 2,045,785 | 6/1936 | Lewis | 568/907 |
| 2,373,359 | 4/1945 | Voogd et al. | 568/886 |
| 2,519,061 | 8/1950 | Mason | 568/907 |
| 2,974,175 | 3/1961 | Watts et al. | 568/907 |
| 3,095,458 | 6/1963 | Judice et al. | 568/890 |
| 4,296,261 | 10/1981 | Carson | 568/889 |

FOREIGN PATENT DOCUMENTS

| | | | |
|---|---|---|---|
| 513390 | 5/1955 | Canada | 568/889 |
| 456547 | 11/1936 | United Kingdom | 568/907 |

Primary Examiner—Joseph E. Evans
Attorney, Agent, or Firm—James R. Hoatson, Jr.; Raymond H. Nelson; William H. Page, II

[57] ABSTRACT

Alcohols may be obtained by an indirect hydration of olefinic hydrocarbons in which said olefinic hydrocarbon is esterified by treatment with an inorganic acid to form dialkyl and alkyl hydrogen salts. The esters are then hydrolyzed with water, the reconstituted acid is stripped by means of a stripping agent such as nitrogen gas, and the resulting alcohols and ethers are recovered. The alcohol production is separated from the dialkyl ether, the latter then being subjected to further treatment such as thermal decomposition and hydrolysis to form an additional amount of the desired alcohol. The reconstituted inorganic acid may be recycled for use as an esterifying agent without having to reconstitute the acid.

11 Claims, 1 Drawing Figure

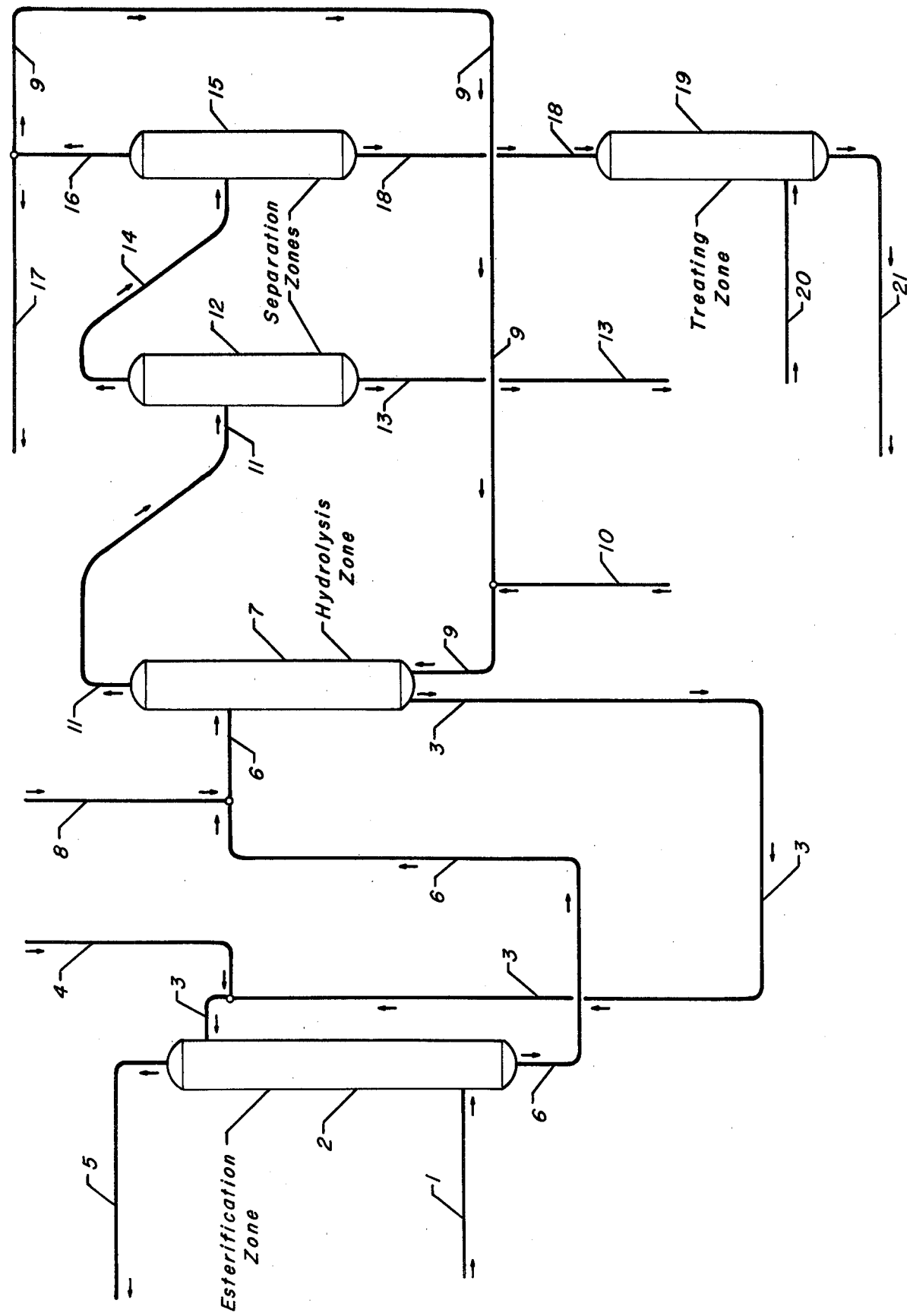

HYDRATION OF OLEFINS

BACKGROUND OF THE INVENTION

The indirect hydration of olefins to alcohols and ethers has employed, in the conventional process, sulfuric acid as the esterification agent to form dialkyl sulfate and alkyl hydrogen sulfate esters. However, in the conventional processes, it is necessary to effect a costly reconcentration or reconstitution of sulfuric acid, the reconcentration resulting from the hydrolysis of the esters with an excess of water in order to prepare the necessary alcohols. The use of alcohols in the chemical industry is well known and covers a wide variety of fields. For example, ethyl alcohol is a staple alcohol of commerce and is used as a solvent, as an intermediate in organic derivatives of dyes, synthetic rugs, synthetic rubber, detergents, surface coatings, cosmetics, pharmaceuticals, explosives, beverages, etc. Likewise, propyl alcohol and especially isopropyl alcohol is used in the manufacture of acetone, as a solvent for essential and other oils, gums, resins, etc., deicing agent for liquid fuels, pharmaceuticals, perfumes, lacquers, etc., while butyl alcohol is used as a solvent in varnish, lacquers, etc. In addition, other alcohols may be used as a component in fuels such as gasoline, etc.

As will hereinafter be shown in greater detail, it has now been discovered that an olefinic hydrocarbon may be hydrated to an alcohol as well as an ether utilizing an inorganic acid as an esterification agent without diluting the acid and eliminating the need for a reconcentration.

SUMMARY OF THE INVENTION

This invention relates to a process for the indirect hydration of an olefinic hydrocarbon to an alcohol. More specifically, the invention is concerned with a process for the indirect hydration of an olefinic hydrocarbon to an alcohol and ether utilizing a concentrated inorganic acid as the primary esterification agent.

As will be shown in greater detail, by utilizing the process conditions and flow scheme of the present process, it has now been discovered that an indirect hydration of an olefinic hydrocarbon to form a desired product may be accomplished in a commercially attractive and economical manner, thus obviating the need for relatively costly equipment and process modification.

It is therefore an object of this invention to provide a process for the indirect hydration of an olefinic hydrocarbon while avoiding the addition of an excess amount of hydrating agent.

A further object of this invention is to provide a process for obtaining alcohols from olefinic hydrocarbons while avoiding the necessity for reconcentrating the esterification agent utilized in said process.

In one aspect an embodiment of this invention is found in a process for the hydration of an olefinic hydrocarbon which comprises esterifying said olefinic hydrocarbon with an inorganic acid at esterification conditions in an esterification zone, subjecting the resultant alkyl salts to hydrolysis by treatment with water at hydration conditions in a hydration zone, stripping the reconstituted inorganic acid from the resultant alcohol and ether hydrolysis product, separating and recovering said alcohol from said ether at separation conditions in a separation zone, treating said ether at treatment conditions in a treatment zone to produce an additional amount of said alcohol, and recovering said alcohol.

A specific embodiment of this invention can be found in a process for the hydration of ethylene which comprises esterifying said ethylene with concentrated sulfuric acid at a temperature in the range of from about 50° to about 150° C. and a pressure in the range of from about 200 to about 1500 psi, subjecting the resultant diethyl sulfate and ethyl hydrogen sulfate to hydrolysis by treatment with water at a temperature in the range of from about ambient to about 200° C. and a pressure in the range of about atmospheric to about 1500 psi, stripping the reconstituted sulfuric acid from the resultant ethyl alcohol and diethyl ether utilizing a stripping gas comprised of nitrogen, separating said ethyl alcohol and said diethyl ether at a temperature in the range of from about ambient to about 200° C. and a pressure in the range of from about atmospheric to about 150 psi, and recovering said ethyl alcohol, treating said diethyl ether by hydrolysis at a temperature in the range of from about 150° to about 250° C. and a pressure in the range of from about subatmospheric to about 1500 psi to produce an additional amount of ethyl alcohol, and recovering the desired ethyl alcohol.

Other objects and embodiments will be found in the following further detailed description of the present invention.

DETAILED DESCRIPTION OF THE INVENTION

As hereinbefore set forth, the present invention is concerned with a process for the indirect hydration of olefinic hydrocarbons to form the corresponding alcohols and ethers utilizing, as an esterification agent, a concentrated inorganic acid. By utilizing the process of this invention, it is possible to avoid the dilution of the acid which is employed as the esterifying agent while achieving a substantially 100% conversion of the water utilized in the hydration reaction. The achievement resulting in the substantially 100% conversion of the water will eliminate the need for a reconcentration of acid, thus needing only a reconstitution of said acid which may be recycled to the esterification zone for further use as the desired agent.

The process described herein involves the utilization of a dilute olefinic hydrocarbon feedstock such as off-gases resulting from a prior refining or reforming operation. The olefins may be present as a mixture of gases containing from 2 to about 4 carbon atoms or more in the chain, specific examples of these olefinic hydrocarbons being ethylene, propylene, butylene, etc. It is also contemplated within the scope of this invention that olefinic hydrocarbons containing more than 4 carbon atoms such as the isomeric amylenes, hexenes, heptenes, octenes, nonenes, decenes, etc. may also be utilized as feedstocks for the preparation of alcohols and ethers.

Examples of inorganic acids which may be employed to effect the esterification step of the present process, preferably in a concentrated state, will include sulfuric acid, sulfurous acid, phosphoric acids such as orthophosphoric acid, pyrophosphoric acid, etc., phosphorous acid, hydrochloric acid, hydrobromic acid, hydroiodic acid, hydrofluoric acid, chlorosulfonic acid, bromosulfonic acid, nitrous acid, boric acid, carbonic acid, iodic acid, the heteropoly acids of tungsten, molybdenum and vanadium such as tungstophosphoric acid, tungstosilicic acid, molybdophosphoric acid, molybdosilicic acid, vanadophosphoric acid, etc.

As an example of the process, when utilizing sulfuric acid as the esterification agent, the feedstock is charged to an esterification zone wherein it is contacted with the esterification agent such as concentrated sulfuric acid, said acid being present in an amount in the range of from about 30% to 97% by weight of the acid solution. The esterification zone is maintained by esterification conditions which will include a temperature in the range of from about 50° to about 150° C. and a pressure in the range of from about 200 to about 1500 pounds per square inch (psi). After allowing the esterification process to proceed for a predetermined period of time, the resulting dialkyl sulfate and alkyl hydrogen sulfate esters are withdrawn from the esterification zone and passed to a hydrolysis and stripping zone along with a stoichiometric amount of water. Any unreacted gases may be vented from the esterification zone for utilization as fuel, etc.

In the hydrolysis and stripping zone, which is maintained by hydrolysis conditions including a temperature range from ambient (20°-25° C.) up to about 200° C. or more and at a pressure ranging from atmospheric to about 1500 psi, the esters are converted to the corresponding alcohols and ethers, while the sulfuric acid is reconstituted. In this hydrolysis zone, the alcohols and ethers are stripped from the acid by means of a stripping gas such as nitrogen which is also charged to the hydrolysis zone. The stripped alcohols and ethers are withdrawn from the hydrolysis zone and passed to at least one separation zone while the reconstituted concentrated sulfuric acid is recycled back to the esterification zone.

In the separation zone, the alcohols and ethers are separated by conventional means such as distillation while employing separation conditions which again include a temperature in the range of from about ambient to about 200° C. while pressures may range from about subatmospheric to about 150 psi. The alcohol which is separated from the ether is recovered, while the ether may, if so desired, be charged to a second separation zone wherein the stripping gas which has passed from the hydrolysis zone along with the alcohol and ether is separated from said ether and reutilized in the hydrolysis zone as a stripping agent.

The ether which has been separated from the stripping gas may then be further treated in a treating zone whereby the ether is converted to the desired alcohol and olefinic hydrocarbons. The treatment of the ether to form the desired alcohol may be effected in either a thermal manner or by hydrolysis. The thermal treatment of the ether to form the alcohol will be effected at treating conditions which will include a temperature in the range of from about 500° to about 750° C. while employing a pressure in the range of from about subatmospheric to about 1500 psi. It is contemplated that the thermal decomposition of the ether to the alcohol and olefinic hydrocarbon may be effected in the presence of an acidic type catalyst which will include such compounds as acidic resins; high surface area inorganic oxides such as alumina, silica-alumina, etc.; zeolites; etc. When utilizing a hydrolysis treatment to form the desired alcohol, the ether will be treated with water at a temperature in the range of from about 150° to about 250° C. utilizing pressures similar to those hereinbefore set forth, that is, from about subatmospheric to about 1500 psi. The olefinic hydrocarbons which are obtained by the decomposition of the ether may then be used as feeds for other processes or, if so desired, may be recycled back to the esterification zone for further treatment with a concentrated sulfuric acid to form the aforementioned sulfate esters.

BRIEF DESCRIPTION OF THE DRAWING

The present process will be further illustrated with reference to the accompanying figure which illustrates a simplified flow diagram of the inventive feature of the present process. Various valves, coolers, condensers, pumps, heaters, controllers, etc. have been eliminated as not being essential to the complete understanding of the present invention. However, the illustration of these, as well as other essential appurtenances will become obvious as the drawing is described.

Referring now to the FIGURE, a feedstock such as an off-gas obtained from a reforming operation containing olefinic hydrocarbon is charged through line 1 to an esterification zone 2. In esterification zone 2, the gas is contacted with an inorganic acid of the type hereinbefore set forth which is charged through line 3 to zone 2. The amount of inorganic acid is predetermined and may require the addition of some make-up acid which is charged through lines 3 & 4 to zone 2. In esterification zone 2, dialkyl salts and, in the event a dibasic acid is employed, alkyl hydrogen salts are formed. Any vent gas which remains is discharged from zone 2 through line 5 and may be used as fuel to form liquid petroleum gas, etc. The dialkyl salt and alkyl hydrogen salt esters which are formed in zone 2 are withdrawn therefrom through line 6 and passed into hydrolysis zone 7 after being admixed with a stoichiometric amount of water which is added through line 8. In hydrolysis zone 7, which is maintained at hydrolysis conditions which include a temperature in the range of from about ambient to about 200° C. and a pressure ranging from atmospheric to about 1500 psi, the aforementioned esters are hydrolyzed and converted to alcohol and dialkyl ether. In addition, the alcohol and ether are stripped from the inorganic acid by means of a stripping gas which, in the preferred embodiment of the invention, comprises nitrogen. The stripping gas is charged to hydrolysis zone 7 through line 9, any make-up stripping gas which is required being added through line 10.

The alcohol and ether which have been formed in hydrolysis zone 7 along with the stripping gas are withdrawn from zone 7 through line 11 and passed to a first separation zone 12 while the stripped acid is recycled to esterification zone 2 through line 3. In separation zone 12, which is maintained at a temperature in the range of from about ambient to about 200° C. and a pressure which may range from subatmospheric up to about 150 psi, the desired alcohol is separated from the dialkyl ether and the stripping gas and withdrawn from separation zone 12 through line 13, following which it is passed to storage. The stripping gas and the dialkyl ether are withdrawn from separation zone 12 through line 14 and passed to a second separation zone 15, which is maintained at similar operating conditions of temperature and pressure. In separation zone 15, the stripping gas is removed over heat through line 16 and recycled back to hydrolysis zone 7 through line 9. If so desired, a portion of the gas may be removed through line 17 and vented or passed to storage.

The dialkyl ether which has been separated from the stripping gas in separation zone 15 is withdrawn from this zone through line 18 and charged to a treating zone 19. In treating zone 19, the dialkyl ether may be treated in either a thermal decomposition manner at temperatures in the range of from about 500° to about 750° C. to form the corresponding alcohol and olefinic hydrocarbon or, alternatively, the ether may be subjected to hydrolysis by treatment with water which, in the event that such a treating system is used, will be charged to treatment zone 19 through line 20. In the event that the ether is subjected to hydrolysis, the hydrolysis conditions which are employed will include a temperature in the range of from 150° to about 250° C. and a pressure ranging from subatmospheric to about 1500 psi. The resulting alcohol and olefinic hydrocarbons are withdrawn from zone 19 through line 21, the alcohol being passed to storage while the olefinic hydrocarbons may be recycled back to esterification zone 2 as a portion of the feedstock or utilized as a feed for other processes.

By utilizing the present process, it is possible to operate the process at a maximum efficiency whereby substantially all of the water is converted, thus obviating the dilution of the inorganic acid with a concurrent avoidance of the necessity of reconcentrating said acid in order that it may be used as an esterification agent.

The following examples are given for purposes of illustrating the process of this invention. However, it is to be understood that these examples are given merely for purposes of illustration and that the present process is not necessarily limited thereto.

EXAMPLE I

In this example, sulfate esters of ethylene were obtained by placing 50.8 grams of 96 wt. % sulfuric acid in a stirred autoclave. A blend gas comprising 18.5% of ethylene and 81.5% nitrogen was charged to the reactor until an initial operating pressure of 450 psi was reached. The autoclave was then heated to a temperature of 100° C. and stirred at a rate of 560 rpm. The reaction was allowed to proceed for a period of 1.3 hours at which time heating was discontinued and the autoclave was allowed to return to room temperature. The excess pressure was discharged, the autoclave was opened and an analysis of the reaction mixture determined that there had been a 97% conversion of the ethylene to form a mixture of diethyl sulfate and ethyl hydrogen sulfate.

EXAMPLE II

To illustrate the hydrolysis of diethyl sulfate, a feed composition of water, sulfuric acid and diethyl sulfate in a molar ratio of 0.15:0.5:1 moles of water to sulfuric acid to diethyl sulfate was placed in an autoclave which was then heated to a temperature of 90° C. Nitrogen, which acted as a stripping gas, was also charged to the autoclave. At the end of 0.2 hour, 78% of the water had been converted with a 58% mole selectivity to ethanol. At 0.75 hour, the water conversion was 76%, while the selectivity to ethanol was 40%. In addition, there was a 60% mole selectivity to diethyl ether.

EXAMPLE III

To illustrate the conversion of diethyl ether to the desired ethanol, 50 grams of diethyl ether along with 61 grams of water, which established a 5:1 moles of water to diethyl ether ratio, were placed in a rotating autoclave. Various catalysts were employed to effect the hydrolysis of the ether, in the first case 10.8 grams of a resin sold under the trade name Amberlite XE-365 was utilized. The autoclave was pressured to 425 psig and heated to a temperature of 200° C. After recovery of the reaction mixture, it was determined that there had been a 26% conversion of the diethyl ether to ethanol. In a similar manner when the water-diethyl ether mixture was subjected to hydrolysis using 10.3 grams of a resin catalyst sold under the trade name Amberlyst 15 at hydrolysis conditions which included a temperature of 158° C. and a pressure of 240 psig, there was only a 3% conversion of the diethyl ether to ethanol. When the hydrolysis reaction was effected in the presence of 5 grams of 12-tungstophosphoric acid at a temperature of 200° C. and a pressure of 425 psig for a period of 6 hours, the conversion of diethyl ether was 18% with a 100% selectivity to ethanol.

I claim as my invention:

1. A process for the hydration of an olefinic hydrocarbon which comprises:
   (a) esterifying said olefinic hydrocarbon with a concentrated inorganic acid at esterification conditions in an esterification zone to produce alkyl salts of said acid;
   (b) hydrolyzing said alkyl salts of said acid by treatment with water at hydration conditions in a hydration zone to form an alcohol and ether hydrolysis product containing reconstituted inorganic acid;
   (c) stripping away alcohol and ether hydrolysis product from said reconstituted inorganic acid and removing said reconstituted inorganic acid from said alcohol and ether hydrolysis product;
   (d) separating said alcohol from said ether of said hydrolysis product in a separation zone at separation conditions to form a product alcohol stream and an ether stream;
   (e) thermally decomposing said ether in a decomposition zone maintained at a temperature in the range of from about 500° C. to about 750° C. and a pressure in the range of from subatmospheric to about 1500 psi to produce an olefinic hydrocarbon and an additional amount of product alcohol;
   (f) recovering said additional amount of product alcohol; and
   (g) recycling at least a portion of said olefinic hydrocarbon produced in thermal decomposition step (e) to said esterification as a part of said olefinic hydrocarbon.

2. The process as set forth in claim 1 in which said esterification conditions include a temperature in the range of from about 50° to about 150° C. and a pressure in the range of from about 200 to about 1500 pounds per square inch.

3. The process as set forth in claim 1 in which said hydration conditions include a temperature in the range of from about ambient to about 200° C. and a pressure in the range of from about atmospheric to about 1500 psi.

4. The process as set forth in claim 1 in which said separation conditions include a temperature in the range of from about ambient to about 200° C. and a pressure in the range of from about subatmospheric to about 150 psi.

5. The process as set forth in claim 1 in which said olefinic hydrocarbon of steps (a) and (e) contains from about 2 to about 4 carbon atoms.

6. The process as set forth in claim 5 in which said olefinic hydrocarbon is ethylene, said alcohol is ethyl alcohol and said ether is diethyl ether.

7. The process as set forth in claim 5 in which said olefinic hydrocarbon is propylene, said alcohol is isopropyl alcohol and said ether is diisopropyl ether.

8. The process as set forth in claim 5 in which said olefinic hydrocarbon is butylene, said alcohol is sec-butyl alcohol and said ether is di-sec-butyl ether.

9. The process as set forth in claim 1 in which said reconstituted inorganic acid is recycled back to said esterification zone.

10. The process as set forth in claim 1 in which said inorganic acid separation from said hydrolysis product is effected by treatment with a stripping gas.

11. The process as set forth in claim 10 in which said stripping gas is nitrogen.

* * * * *